United States Patent
Fageon et al.

(10) Patent No.: US 9,855,449 B2
(45) Date of Patent: Jan. 2, 2018

(54) COSMETIC COMPOSITION COMPRISING A SUPERABSORBENT POLYMER AND A LAMELLAR OR PLATELET-SHAPED MATTING MINERAL FILLER

(71) Applicant: L'OREAL, Paris (FR)

(72) Inventors: Laure Fageon, Paris (FR); Raluca Lorant, Thiais (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/365,257

(22) PCT Filed: Dec. 17, 2012

(86) PCT No.: PCT/EP2012/075777
§ 371 (c)(1),
(2) Date: Jun. 13, 2014

(87) PCT Pub. No.: WO2013/087928
PCT Pub. Date: Jun. 20, 2013

(65) Prior Publication Data
US 2014/0302159 A1  Oct. 9, 2014

(30) Foreign Application Priority Data
Dec. 16, 2011  (FR) ..................... 11 61792

(51) Int. Cl.
| | | |
|---|---|---|
| *A61Q 19/00* | (2006.01) | |
| *A61K 8/02* | (2006.01) | |
| *A61K 8/06* | (2006.01) | |
| *A61K 8/25* | (2006.01) | |
| *A61Q 9/00* | (2006.01) | |
| *A61K 8/81* | (2006.01) | |

(52) U.S. Cl.
CPC ............ *A61Q 19/002* (2013.01); *A61K 8/025* (2013.01); *A61K 8/0254* (2013.01); *A61K 8/25* (2013.01); *A61K 8/8147* (2013.01); *A61Q 9/00* (2013.01); *A61Q 19/00* (2013.01); *A61Q 19/008* (2013.01); *A61K 2800/412* (2013.01); *A61K 2800/546* (2013.01)

(58) Field of Classification Search
CPC ........ A61K 8/25; A61K 8/8147; A61K 8/025; A61K 8/0254; A61Q 19/00; A61Q 19/008; A61Q 19/10
See application file for complete search history.

(56) References Cited

U.S. PATENT DOCUMENTS

| | | | | |
|---|---|---|---|---|
| 2002/0039976 | A1* | 4/2002 | Sebillotte-Arnaud et al. | ............ 510/119 |
| 2004/0265347 | A1* | 12/2004 | Auguste et al. | ............. 424/401 |
| 2008/0008678 | A1* | 1/2008 | Wyers | ......... 424/78.09 |
| 2008/0108534 | A1* | 5/2008 | Bernard et al. | ............. 510/119 |
| 2010/0330018 | A1* | 12/2010 | Lorant | ........... A61K 8/025 424/70.9 |
| 2011/0014138 | A1* | 1/2011 | Romaine | ............ A61K 8/06 424/59 |
| 2012/0003284 | A1* | 1/2012 | Arnaud | ............. A61K 8/0229 424/401 |

FOREIGN PATENT DOCUMENTS

| | | | | |
|---|---|---|---|---|
| EP | 1800661 A1 * | 6/2007 | | |
| WO | WO 2010054921 A1 * | 5/2010 | ........... A61K 8/0229 | |

OTHER PUBLICATIONS

Technical Absorbents, SAF Technical Datasheets, 2014.*
ImerCare, Technical Information, Imerys Performance (first ed. Feb. 2011).*

* cited by examiner

*Primary Examiner* — Gina C Justice
(74) *Attorney, Agent, or Firm* — Polsinelli PC

(57) ABSTRACT

The present invention relates to a composition for topical application, comprising at least one aqueous phase, at least one superabsorbent polymer and at least one lamellar or platelet-shaped matting mineral filler. A subject of the invention is also a cosmetic treatment process for keratin materials, which consists in applying to the keratin materials a composition as defined above, and also the use of this composition in the cosmetic or dermatological field, and in particular for caring for, protecting and/or making up bodily or facial skin, or for haircare. The composition according to the invention has both a matt appearance throughout all the steps of its use, from the appearance of the product up to the finished skin, and a comfortable sensation throughout its use, from the application to the total penetration of the product.

17 Claims, No Drawings

COSMETIC COMPOSITION COMPRISING A SUPERABSORBENT POLYMER AND A LAMELLAR OR PLATELET-SHAPED MATTING MINERAL FILLER

CROSS REFERENCE TO RELATED APPLICATIONS

This application is a National Phase filing under 35 U.S.C. §371 of PCT/EP2012/075777 filed on Dec. 17, 2012; and this application claims priority to Application No. 1161792 filed in France on Dec. 16, 2011, and this application claims the benefit of U.S. Provisional Application No. 61/578,190 filed on Dec. 20, 2014; the entire contents of each application is hereby incorporated by reference.

The present patent application relates to a composition for topical application comprising at least one aqueous phase, at least one superabsorbent polymer and at least one lamellar or platelet-shaped matting mineral filler, and to the use of the said composition in cosmetics and dermatology, in particular for caring for or treating keratin materials.

Fillers are commonly used in cosmetics to afford perceptible benefits on the skin such as a matting effect, unification of the complexion, or alternatively the absorption of sebum and/or of excess skin moisture. These products are particularly pertinent for treating greasy and shiny skin.

However, the introduction of fillers, in particular lamellar or platelet-shaped fillers, leads to impairment of the sensory properties, and in particular of the comfort during and after application.

Moreover, the appearance of the product and of the skin during the application of the product is also an important criterion to be taken into consideration, since this has a substantial influence on the perception of efficacy.

When designing products, the formulator must take care to ensure that there is coherence between the look of the product (whether in its conditioning or on the skin during its use) and the promised efficacy on the skin, in order to reinforce the overall perception of efficacy and the consumer's satisfaction.

Thus, when designing a matting product, it is desirable for the product to have a matt appearance throughout all the steps of its use.

There is thus still a need to make compositions that have both a matt appearance throughout all the steps of its use, from the appearance of the product up to the finished skin, and a comfortable sensation throughout its use, from the application to the total penetration of the product.

The Applicant has discovered that cosmetic compositions comprising an aqueous phase, a superabsorbent polymer and a lamellar or platelet-shaped matting mineral filler can produce products that are both comfortable and matt throughout their use.

Thus, one subject of the present invention is a composition for topical application, comprising at least one aqueous phase, at least one superabsorbent polymer and at least one lamellar or platelet-shaped matting mineral filler.

Since the composition of the invention is intended for topical application to the skin or the integuments, it comprises a physiologically acceptable medium, i.e. a medium that is compatible with all keratin materials such as the skin, the nails, mucous membranes and keratin fibres (such as the hair or the eyelashes).

The composition according to the invention has both a matt appearance throughout all the steps of its use, from the appearance of the product up to the finished skin, and a comfortable sensation throughout its use, from the application to the total penetration of the product.

A subject of the invention is also a cosmetic treatment process for keratin materials, which consists in applying to the keratin materials a composition as defined above.

A subject of the invention is also the use of the said composition in the cosmetic or dermatological field, and in particular for caring for, protecting and/or making up bodily or facial skin, or for haircare.

In the text hereinbelow, the expression "at least one" is equivalent to "one or more" and, unless otherwise indicated, the limits of a range of values are included in that range.

Superabsorbent Polymers

The term "superabsorbent polymer" means a polymer that is capable in its dry form of spontaneously absorbing at least 20 times its own weight of aqueous fluid, in particular of water and especially distilled water. Such superabsorbent polymers are described in the publication "Absorbent polymer technology, Studies in polymer science 8" by L. Brannon-Pappas and R. Harland, published by Elsevier, 1990.

These polymers have a large capacity for absorbing and retaining water and aqueous fluids. After absorption of the aqueous liquid, the polymer particles thus engorged with aqueous fluid remain insoluble in the aqueous fluid and thus conserve their individualized particulate state.

The superabsorbent polymer may have a water-absorbing capacity ranging from 20 to 2000 times its own weight (i.e. 20 g to 2000 g of absorbed water per gram of absorbent polymer), preferably from 30 to 1500 times and better still from 50 to 1000 times. These water absorption characteristics are defined under standard temperature (25° C.) and pressure (760 mmHg, i.e. 100 000 Pa) conditions and for distilled water.

The value of the water-absorbing capacity of a polymer may be determined by dispersing 0.5 g of polymer(s) in 150 g of a water solution, waiting for 20 minutes, filtering the unabsorbed solution through a 150 µm filter for 20 minutes and weighing the unabsorbed water.

The superabsorbent polymer used in the composition of the invention is in the form of particles. Preferably, the superabsorbent polymer has, in the dry or nonhydrated state, an average size of less than or equal to 100 µm, preferably less than or equal to 50 µm, ranging for example from 10 to 100 µm, preferably from 15 to 50 µm, and better still from 20 to 30 µm.

The average size of the particles corresponds to the weight-average diameter ($D_{50}$) measured by laser particle size analysis or another equivalent method known to those skilled in the art.

These particles, once hydrated, swell and form soft particles which have an average size that can range from 10 µm to 1000 µm, preferably from 20 µm to 500 µm, and more preferably from 50 µm to 400 µm.

Preferably, the superabsorbent polymers used in the present invention are in the form of spherical particles.

Mention may be made especially of absorbent polymers chosen from:
   crosslinked sodium polyacrylates, for instance those sold under the brand names Octacare X100, X110 and RM100 by the company Innospec Active Chemicals, those sold under the names Flocare GB300 and Flosorb 500 by the company SNF, those sold under the names Luquasorb 1003, Luquasorb 1010, Luquasorb 1280 and Luquasorb 1110 by the company BASF, those sold under the names Water Lock G400 and G430 (INCI name: Acrylamide/Sodium acrylate copolymer) by the company Grain Processing, or else Aqukeep® 10 SH NF proposed by the company Sumitomo Seika, starches grafted with an acrylic polymer (homopolymer or copolymer) and in particular with sodium polyacrylate, such as those sold under the name Sanfresh ST-100MC by the company Sanyo Chemical Industries or Makimousse 25 or Makimousse 12 by the company Daito Kasei (INCI name: Sodium polyacrylate starch), hydrolysed starches grafted with an acrylic polymer (homopolymer or copolymer) and especially acryloacrylamide/sodium acrylate copolymer, such as those sold under the names Water Lock A-240, A-180, B-204, D-223, A-100, C-200 and D-223 by the company Grain Processing (INCI name: Starch/acrylamide/sodium acrylate copolymer), polymers based on starch, gum and cellulose derivative, such as the product containing starch, guar gum and sodium carboxymethylcellulose, sold under the name Lysorb 220 by the company Lysac, and mixtures thereof.

The superabsorbent polymers used in the present invention may be crosslinked or noncrosslinked. They are preferably chosen from crosslinked polymers.

The superabsorbent polymers used in the present invention are preferably crosslinked acrylic homopolymers or copolymers, which are preferably neutralized, and which are in particulate form.

Preferably, the superabsorbent polymer is chosen from crosslinked sodium polyacrylates, preferably in the form of particles with an average size (or average diameter) of less than or equal to 100 microns, more preferably in the form of spherical particles. These polymers preferably have a capacity to absorb water at 0.9% of NaCl from 10 to 100 g/g, preferably from 20 to 80 g/g and better still from 30 to 80 g/g.

The superabsorbent polymer may be present in the composition according to the invention in an active material content ranging, for example, from 0.05% to 15% by weight, preferably from 0.1% to 10% by weight, preferably ranging from 0.1% to 5% by weight, preferentially ranging from 0.1% to 3% by weight or even from 0.1% to 2% by weight relative to the total weight of the composition.

Lamellar or Platelet-Shaped Matting Mineral Fillers

In the context of the invention, the term "mineral filler" means solid mineral particles, i.e. solid non-organic particles.

The term "lamellar particles" or "platelet-shaped particles" means particles of parallelepipedal shape (rectangular or square surface), discoid shape (circular surface) or ellipsoid shape (oval surface), characterized by three dimensions: a length, a width and a height, these particles being insoluble in the medium of the composition according to the invention, even at the melting point of the medium (about 100° C.).

When the shape is circular, the length and the width are identical and correspond to the diameter of a disc, whereas the height corresponds to the thickness of the disc. When the surface is oval, the length and the width correspond, respectively, to the large axis and the small axis of an ellipse and the height corresponds to the thickness of the elliptic disc formed by the platelet. When it is a parallelepiped, the length and the width may be of identical or different dimensions: when they are of the same dimension, the shape of the surface of the parallelepiped is a square; in the contrary case, the shape is rectangular. As regards the height, it corresponds to the thickness of the parallelepiped.

The length of the lamellar particles used according to the invention preferably ranges from 0.01 to 100 µm, better still from 0.1 to 50 µm and even better still from 1 to 50 µm. The width of these platelets preferably ranges from 0.01 to 100 µm, better still from 0.1 to 50 µm and even better still from 1 to 10 µm. The height (thickness) of these platelets preferably ranges from 0.1 nm to 1 µm (0.1 to 1000 nm), better still from 1 nm to 600 nm and even better still from 1 nm to 500 nm.

The term "matting filler" means a filler with a refractive index of less than or equal to 1.55. As lamellar or platelet-shaped matting mineral fillers that may be used in the composition of the invention, mention may be made of silicas, and in particular porous silica microparticles such as the Silica Beads® SB 150 and SB 700 from Miyoshi Kasei with a mean size of 5 µm and the Sunsphere® series H from Asahi Glass, such as H33 and H51 with mean sizes, respectively, of 3.5 and 5 µm.

As lamellar or platelet-shaped matting mineral fillers that may be used in the composition of the invention, mention may also be made of silicates such as those chosen from montmorillonites, kaolinites, smectites, talcs, perlites and expanded perlites, and mixtures thereof.

Montmorillonites and smectites are hydrated magnesium aluminium silicates. Examples that may be mentioned include the montmorillonite sold under the name Gel White H by the company Rockwood Additives, and the purified smectites sold under the name Veegum Granules by the company Vanderbilt.

Kaolinites are hydrated aluminium silicates. Examples that may be mentioned include the kaolins sold under the names Coslin C 100 by the company BASF Personal Care Ingredients or Kaolin Supreme by the company Imerys.

Talcs are hydrated magnesium silicates usually comprising aluminium silicate. The crystal structure of talc consists of repeated layers of a sandwich of brucite between layers of silica. Examples that may be mentioned include micronized magnesium silicate with a particle size of 5 microns, sold under the name Micro Ace P3 by the company Nippon Talc, or the talcs sold under the names Rose Talc and Talc SG-2000 by the company Nippon Talc, J 68 BC by the company US Cosmetics (Miyoshi), Lyzenac 00 and Luzenac Pharma M by the company Luzenac, and Talc JA-46R by the company Asada Milling.

The perlites that may be used in the context of the invention may be expanded perlites. They are generally aluminosilicates of volcanic origin and have the composition:

70.0-75.0% by weight of silica $SiO_2$;
12.0-15.0% by weight of oxide of aluminium oxide $Al_2O_3$;
3.0-5.0% of sodium oxide $Na_2O$;
3.0-5.0% of potassium oxide $K_2O$;
0.5-2% of iron oxide $Fe_2O_3$;
0.2-0.7% of magnesium oxide MgO;
0.5-1.5% of calcium oxide CaO;
0.05-0.15% of titanium oxide $TiO_2$, The perlite is ground, dried and then calibrated in a first step. The product obtained, known as perlite ore, is grey-coloured and has a size of about 100 µm.

The perlite ore is then expanded (1000° C./2 seconds) to give more or less white particles. When the temperature reaches 850-900° C., the water trapped in the structure of the material evaporates and brings about the expansion of the material relative to its original volume. The expanded perlite particles in accordance with the invention may be obtained via the expansion process described in U.S. Pat. No. 5,002, 698.

According to one particular embodiment of the invention, the perlite particles used are ground: in this case, they are known as Expanded Milled Perlite (EMP). They preferably have a particle size defined by a median diameter $D_{50}$ ranging from 0.5 to 50 µm and preferably from 0.5 to 40 µm.

Examples that may be mentioned include the perlites sold under the names Optimat 1430 OR and Optimat 2550 OR by the company World Minerals.

Preferably, the perlite particles used have an untamped apparent density at 25° C. ranging from 10 to 400 kg/m$^3$ (standard DIN 53468) and preferably from 10 to 300 kg/m$^3$.

According to one particular embodiment of the present invention, the particles are chosen from particles with a water absorption capacity, measured at the wet point, of greater than or equal to 100 g, preferably ranging from 200% to 1500% and even more preferentially from 250% to 800%.

The wet point corresponds to the amount of water that needs to be added to 100 g of particles in order to obtain a homogeneous paste. This method is derived directly from that of the oil uptake applied to solvents.

According to one preferred embodiment of the invention, the lamellar or platelet-shaped matting mineral fillers are chosen from expanded perlites and silicas.

The lamellar or platelet-shaped matting mineral filler(s) may be present in the composition according to the invention in an active material content ranging, for example, from 0.05% to 10% by weight, preferably ranging from 0.1% to 5% by weight and preferentially ranging from 0.1% to 3% by weight relative to the total weight of the composition.

The composition according to the invention may be in various galenical forms conventionally used for topical applications and especially in the form of dispersions of the lotion or serum type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type. These compositions are prepared according to the usual methods.

According to one preferred embodiment of the invention, the composition is in the form of an emulsion and especially an oil-in-water emulsion or a water-in-oil emulsion.

In addition, the compositions used according to the invention may be more or less fluid and may have the appearance of a white or coloured cream, an ointment, a milk, a lotion, a serum, a paste or a mousse.

The composition preferably exhibits a skin-friendly pH which generally ranges from 3 to 8 and preferably from 4.5 to 7.

Aqueous Phase

The aqueous phase of the composition in accordance with the invention comprises at least water. According to the galenical form of the composition, the amount of aqueous phase can range from 0.1% to 99% by weight, preferably from 0.5% to 98% by weight, better still from 30% to 95% by weight and even better still from 40% to 95% by weight, relative to the total weight of the composition. This amount depends on the desired galenical form of the composition. The amount of water can represent all or a portion of the aqueous phase and it is generally at least 30% by weight relative to the total weight of the composition, preferably at least 50% by weight, better still at least 60% by weight.

The aqueous phase may comprise at least one hydrophilic solvent, for instance substantially linear or branched lower monoalcohols containing from 1 to 8 carbon atoms, for instance ethanol, propanol, butanol, isopropanol or isobutanol; polyols such as propylene glycol, isoprene glycol, butylene glycol, glycerol, sorbitol or polyethylene glycols and derivatives thereof, and mixtures thereof.

Fatty Phase

When it is in the form of an emulsion, the composition according to the invention may comprise a fatty phase. The proportion of the fatty phase of the emulsion can range, for example, from 1 to 80% by weight, preferably from 2 to 50% by weight and better still from 5 to 30% by weight, relative to the total weight of the composition.

The nature of the fatty phase of the composition is not critical. The fatty phase may thus consist of any fatty substance conventionally used in the cosmetic or dermatological fields; it comprises in particular at least one oil (fatty substance that is liquid at 25° C.).

Mention may be made, as oils which can be used in the composition of the invention, for example, of:

hydrocarbon-based oils of animal origin, such as perhydrosqualene;

hydrocarbon oils of vegetable origin, such as liquid triglycerides of fatty acids comprising from 4 to 10 carbon atoms, such as heptanoic or octanoic acid triglycerides, or alternatively, for example, sunflower oil, maize oil, soybean oil, cucumber oil, grape seed oil, sesame seed oil, hazelnut oil, apricot oil, macadamia oil, arara oil, castor oil, avocado oil, caprylic/capric acid triglycerides, such as those sold by Stearineries Dubois or those sold under the names Miglyol 810, 812 and 818 by Dynamit Nobel, jojoba oil and shea butter oil;

synthetic esters and ethers, in particular of fatty acids, such as oils of formulae $R^aCOOR^b$ and $R^aOR^b$ in which $R^a$ represents the residue of a fatty acid comprising from 8 to 29 carbon atoms and $R^b$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate, fatty alcohol heptanoates, octanoates and decanoates; polyol esters, such as propylene glycol dioctanoate, neopentyl glycol diheptanoate and diethylene glycol diisononanoate; and pentaerythritol esters, such as pentaerythrityl tetraisostearate;

substantially linear or branched hydrocarbons of mineral or synthetic origin, such as volatile or non-volatile liquid paraffins, and derivatives thereof, petroleum jelly, polydecenes, isohexadecane, isododecane, and hydrogenated polyisobutene such as Parleam® oil;

fatty alcohols having from 8 to 26 carbon atoms, such as cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol;

alkoxylated and in particular ethoxylated fatty alcohols, such as oleth-12, ceteareth-12 and ceteareth-20;

partially hydrocarbon-based and/or silicone-based fluoro oils, such as those described in the document JP-A-2-295 912. Fluoro oils that may also be mentioned include perfluoromethylcyclopentane and perfluoro-1, 3-dimethylcyclohexane, sold under the names Flutec PC1® and Flutec PC3® by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane sold under the name MSX 4518 by the company 3M and nonafluoroethoxyisobutane; perfluoromorpholine derivatives such as 4-trifluoromethylperfluoromorpholine sold under the name PF 5052® by the company 3M;

silicone oils, for instance volatile or non-volatile polymethylsiloxanes (PDMS) with a substantially linear or cyclic silicone chain, which are liquid or pasty at room temperature, especially cyclopolydimethylsiloxanes (cyclomethicones) such as cyclohexadimethylsiloxane and cyclopentadimethylsiloxane; polydimethylsiloxanes comprising alkyl, alkoxy or phenyl groups, which are pendent or at the end of a silicone chain, these groups containing from 2 to 24 carbon atoms; phenylsilicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes;

mixtures thereof.

In the list of the abovementioned oils, the term "hydrocarbon oil" is understood to mean any oil predominantly comprising carbon and hydrogen atoms, and optionally ester, ether, fluoro, carboxylic acid and/or alcohol groups.

The emulsions generally contain at least one emulsifier chosen from amphoteric, anionic, cationic or nonionic emulsifiers, used alone or as a mixture. The emulsifiers are appropriately chosen according to the emulsion to be obtained (W/O or O/W).

The emulsifiers are generally present in the composition in a proportion ranging from 0.1% to 30% by weight and preferably from 0.2% to 20% by weight relative to the total weight of the composition.

For the W/O emulsions, examples of emulsifiers that may be mentioned include dimethicone copolyols such as the mixture of cyclomethicone and of dimethicone copolyol sold under the name DC 5225 C by the company Dow Corning, and alkyl dimethicone copolyols such as the laurylmethicone copolyol sold under the name Dow Corning 5200 Formulation Aid by the company Dow Corning and the cetyl dimethicone copolyol sold under the name Abil EM 90® by the company Goldschmidt, or the mixture polyglyceryl-4 isostearate/cetyl dimethicone copolyol/hexyl laurate sold under the name Abil WE 09 by the company Goldschmidt. One or more co-emulsifiers may also be added thereto. The co-emulsifier may be chosen advantageously from the group comprising polyol alkyl esters. Polyol alkyl esters that may especially be mentioned include glycerol and/or sorbitan esters, for example the polyglyceryl isostearate, such as the product sold under the name Isolan GI 34 by the company Goldschmidt, sorbitan isostearate, such as the product sold under the name Arlacel 987 by the company ICI, sorbitan glyceryl isostearate, such as the product sold under the name Arlacel 986 by the company ICI, and mixtures thereof.

Examples of emulsifiers that may be mentioned for the O/W emulsions include nonionic surfactants, and especially esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof; the polyethylene glycol esters of $C_8$-$C_{24}$ fatty acids, and the oxyalkylenated derivatives thereof; the sorbitol esters of $C_8$-$C_{24}$ fatty acids, and the oxyalkylenated derivatives thereof; fatty alcohol ethers; the sugar ethers of $C_8$-$C_{24}$ fatty alcohols, and mixtures thereof.

Glyceryl esters of fatty acids that may especially be mentioned include glyceryl stearate (glyceryl monostearate, distearate and/or tristearate) (CTFA name: glyceryl stearate) or glyceryl ricinoleate, and mixtures thereof.

Polyethylene glycol esters of fatty acids that may especially be mentioned include polyethylene glycol stearate (polyethylene glycol monostearate, distearate and/or tristearate) and more especially polyethylene glycol 50 OE monostearate (CTFA name: PEG-50 stearate) and polyethylene glycol 100 OE monostearate (CTFA name: PEG-100 stearate), and mixtures thereof.

Mixtures of these surfactants may also be used, for instance the product containing glyceryl stearate and PEG-100 stearate, sold under the name Arlacel 165 by the company Uniqema, and the product containing glyceryl stearate (glyceryl mono-distearate) and potassium stearate, sold under the name Tegin by the company Goldschmidt (CTFA name: glyceryl stearate SE).

Examples of fatty alcohol ethers that may be mentioned include polyethylene glycol ethers of fatty alcohols containing from 8 to 30 carbon atoms and especially from 10 to 22 carbon atoms, such as polyethylene glycol ethers of cetyl alcohol, of stearyl alcohol or of cetearyl alcohol (mixture of cetyl alcohol and stearyl alcohol). Examples that may be mentioned include ethers comprising from 1 to 200 and preferably from 2 to 100 oxyethylene groups, such as those of CTFA name Ceteareth-20 and Ceteareth-30, and mixtures thereof.

Examples of sugar mono- or polyalkyl esters or ethers that may be mentioned include the methylglucose isostearate sold under the name Isolan-IS by the company Degussa Goldschmidt, or else the sucrose distearate sold under the name Crodesta F50 by the company Croda, and the sucrose stearate sold under the name Ryoto sugar ester S 1570 by the company Mitsubishi Kagaku Foods.

Mention may also be made of lipoamino acids and salts thereof, such as monosodium and disodium acylglutamates, for instance the monosodium stearoyl glutamate sold under the name Amisoft HS-11PF and the disodium stearoyl glutamate sold under the name Amisoft HS-21P by the company Ajinomoto.

In a known manner, all the compositions of the invention may contain one or more adjuvants that are common in cosmetics and dermatology: hydrophilic or lipophilic gelling agents and/or thickeners; moisturizers; emollients; hydrophilic or lipophilic active agents; free-radical scavengers; sequestrants; antioxidants; preserving agents; acidifying or basifying agents; fragrances; film-forming agents; dyestuffs (pigments such as iron oxides and titanium dioxide, nacres, soluble dyes), and fillers other than those defined previously; and mixtures thereof.

The amounts of these various adjuvants are those conventionally used in the fields under consideration. In particular, the amounts of active agents vary according to the desired objective and are those conventionally used in the fields under consideration, and for example from 0.1% to 20%, and preferably from 0.5% to 10% by weight of the total weight of the composition.

Active Agents

Non-limiting examples of active agents that may be mentioned include ascorbic acid and derivatives thereof such as 5,6-di-O-dimethylsilyl ascorbate (sold by the company Exsymol under the reference Pro-AA), D,L-α-tocopheryl-21-ascorbyl phosphate potassium salt (sold by the company Senju Pharmaceutical under the reference Sepivital EPC), magnesium ascorbyl phosphate, sodium ascorbyl phosphate (sold by the company Roche under the reference Stay-C 50); phloroglucinol; enzymes; and mixtures thereof. According to one preferred embodiment of the invention, ascorbic acid is used among the oxidation-sensitive hydrophilic active agents. The ascorbic acid may be of any nature. Thus, it may be of natural origin in powder form or in the form of orange juice, preferably orange juice concentrate. It may also be of synthetic origin, preferably in powder form.

As other active agents that may be used in the composition of the invention, examples that may be mentioned include moisturizing agents, such as protein hydrolysates and polyols, for instance glycerol, glycols, for instance polyethylene glycols; natural extracts; anti-inflammatory agents; oligomeric proanthocyanidins; vitamins such as vitamin A (retinol), vitamin E (tocopherol), vitamin B5 (panthenol), vitamin B3 (niacinamide), derivatives of these vitamins (in particular esters) and mixtures thereof; urea; caffeine; depigmenting agents such as kojic acid, hydroquinone and caffeic acid; salicylic acid and derivatives thereof; α-hydroxy acids, such as lactic acid and glycolic acid and derivatives thereof; retinoids, such as carotenoids and vitamin A derivatives; hydrocortisone; melatonin; extracts of algae, of fungi, of plants, of yeasts, of bacteria; steroids; antibacterial active agents, such as 2,4,4'-trichloro-2'-hydroxydiphenyl ether (or triclosan), 3,4,4'-trichlorocarbanilide (or triclocarban) and the acids indicated above, and in particular salicylic acid and derivatives thereof; matting agents, for instance fibres; tensioning agents; UV-screening agents; and mixtures thereof.

Needless to say, a person skilled in the art will take care to select the optional adjuvant(s) added to the composition according to the invention such that the advantageous properties intrinsically associated with the composition in accordance with the invention are not, or are not substantially, adversely affected by the envisaged addition.

The examples that follow will allow the invention to be understood more clearly, without, however, being limiting in nature. The amounts indicated are given as weight percentages of active material, unless otherwise mentioned. The names of the compounds are indicated as INCI names.

EXAMPLES

For all the compositions made, the following parameters were evaluated:

Matt Appearance

The matt appearance of the products and of the skin is evaluated:
- in the conditioning
- during spreading onto the skin
- at the end of application (before total drying)
- 2 minutes after total penetration.

The reflection of the product is defined on a scale from very matt to very glossy: very matt; matt; quite matt; glossy; very glossy.

Comfort

The comfort of the products on the skin is evaluated 2 minutes after total penetration. On a scale ranging from Not, sparingly, moderately, quite and very.

These parameters were evaluated visually and by touch by a panel of 10 experts, according to the following protocol.

The panel of experts trained in the description of care products evaluates the formulations monadically. The products are conditioned in standard 15 ml transparent jars that are coded. Within the same session, the samples are presented in random order to each panelist. 0.05 ml of product is applied to the top half of the hand (washed beforehand with water and liquid soap and wiped with a paper handkerchief) and then spread out (10 passes with the index and major fingers).

Comparative Examples: Matting Emulsion

|  | A* | B |
|---|---|---|
| PHASE A |  |  |
| Water | qs 100 | qs 100 |
| Preserving agent(s) | 0.4 | 0.4 |
| PHASE B |  |  |
| Glycerol | 7 | 7 |
| Sodium acrylates crosspolymer-2 (and) water (and) silica (Aquakeep ® 10 SH NF sold by the company Sumimoto Seika) | 0.8 | — |
| Sodium polyacrylate (Cosmedia SP ® sold by the company Cognis) | — | 0.8 |
| PHASE C |  |  |
| Dicaprylyl carbonate | 10 | 10 |
| Inulin lauryl carbamate (Inutec SP1 from Beneo Bio Based Chemicals) | 0.2 | 0.2 |
| PHASE D |  |  |
| Perlite (Optimat 2550 OR sold by the company World Minerals) | 1 | 1 |
| PHASE E |  |  |
| Denatured alcohol | 5 | 5 |
| Fragrance | 0.1 | 0.1 |

*Composition according to the invention

Manufacturing Process

Heat phase A up to 80° C. to dissolve the preserving agents. Cool to 70° C. and add phase B while mixing with a Rayneri blender. Homogenize until a homogeneous gel is obtained and add phase C, while mixing with a Rayneri blender, at about 50° C. Cool to room temperature and add phases D and E.

Evaluation

Matt Effect:

Emulsion A: According to the Invention

8/10 of the volunteers considered the product to be from very matt to matt over all the steps of its use.

2/10 considered the product to be matt over all the steps of its use, except at the end of application, where the product was judged to be quite matt.

Emulsion B: Outside the Invention

9/10 of the volunteers considered the product to be very glossy over all the steps of its use before the total penetration and quite matt 2 minutes after penetration.

1/10 of the volunteers considered the product to be glossy over all the steps of its use before the total penetration and quite matt 2 minutes after penetration.

Comfort:

Emulsion A: According to the Invention

9/10 of the volunteers considered the product to be "very" comfortable.

1/10 of the volunteers considered the product to be "quite" comfortable.

Emulsion B: Outside the Invention

8/10 of the volunteers considered the product to be "sparingly" comfortable.

2/10 of the volunteers considered the product to be "quite" comfortable.

Thus, composition A according to the invention is judged to be both more matt and more comfortable than composition B outside the invention.

Example According to the Invention: Moisturizing Cream for Greasy Skin

| Composition | C |
|---|---|
| PHASE A | |
| Water | qs 100 |
| Preserving agent(s) | 0.4 |
| PHASE B | |
| Glycerol | 10 |
| Sodium acrylates crosspolymer-2 (and) water (and) silica (Aquakeep ® 10 SH NF sold by the company Sumimoto Seika) | 0.8 |
| PHASE C | |
| Polydimethylsiloxane 5 cSt | 5 |
| Isohexadecane | 5 |
| Inulin lauryl carbamate (Inutec SP1 from Beneo Bio Based Chemicals) | 0.2 |
| PHASE D | |
| Perlite (Optimat 2550 OR sold by the company World Minerals) | 1 |
| PHASE E | |
| Denatured alcohol | 7 |
| Fragrance | 0.1 |

Manufacturing Process

Heat phase A up to 80° C. to dissolve the preserving agents. Cool to 70° C. and add phase B while mixing with a Rayneri blender. Homogenize until a homogeneous gel is obtained and add phase C, while mixing with a Rayneri blender, at about 50° C. Cool to room temperature and add phases D and E.

Results

The formulation is quite matt in appearance, until after application. It is judged to be comfortable.

Example According to the Invention: Matt-Effect After-Shave Serum for Men

| Composition | D |
|---|---|
| PHASE A | |
| Water | qs 100 |
| Preserving agent(s) | 0.4 |
| PHASE B | |
| Caprylic/capric triglyceride (and) sodium acrylate copolymer (Luvigel EM ® sold by the company BASF) | 2 |
| PHASE C | |
| Glycerol | 7 |
| Sodium acrylates crosspolymer-2 (and) water (and) silica (Aquakeep ® 10 SH NF sold by the company Sumimoto Seika) | 0.4 |
| PHASE C | |
| Isohexadecane | 2 |
| PHASE D | |
| Silica (Sunsphere H51 sold by the company AGC SI-Tech) | 1 |
| Perlite (Optimat 2550 OR from World Minerals) | 1 |

| Composition | D |
|---|---|
| PHASE E | |
| Denatured alcohol | 5 |
| Fragrance | 0.1 |

Manufacturing Process

Heat phase A up to 80° C. to dissolve the preserving agents. Cool to 70° C. and add phase B while mixing with a Rayneri blender. Homogenize until a homogeneous gel is obtained and add phase C, while mixing with a Rayneri blender, at about 50° C. Cool to room temperature and add phases D and E.

Results

The formulation is quite matt in appearance, until after application. It is judged to be comfortable.

Example According to the Invention: Moisturizing Cream

| Composition | E |
|---|---|
| PHASE A | |
| Disodium EDTA | 0.1 |
| Water | qs 100 |
| Glycerol | 7 |
| Preserving agent(s) | 1 |
| PHASE B | |
| Cetyl alcohol | 0.5 |
| Isopropyl lauroyl sarcosinate | 5 |
| Hydrogenated polyisobutene | 4 |
| Lipophilic thickener(s) | 2 |
| Behenyl alcohol (and) glyceryl stearate (and) disodium ethylene dicocamide PEG-15 disulfate (and) glyceryl stearate citrate (Ceralution H from Sasol) | 2 |
| PHASE C | |
| Silica (Silica beads SB 700 sold by the company Miyoshi Kasei) | 0.5 |
| Sodium acrylates crosspolymer-2 (and) water (and) silica (Aquakeep ® 10 SH NFC sold by the company Sumimoto Seika) | 0.8 |

Manufacturing Process

Heat phase A up to 80° C. to dissolve the preserving agents. Cool to 70° C. Heat phase B to 80° C. Add phase B while mixing with an Ultra-Turrax blender. Homogenize until a homogeneous emulsion is obtained and add phase C, while mixing with a Rayneri blender, at about 50° C.

Results

The formulation is quite matt in appearance, until after application. It is judged to be comfortable.

The invention claimed is:

1. A composition for topical application, comprising at least one aqueous phase, 0.05% to 15% of at least one superabsorbent polymer, wherein the at least one superabsorbent polymer is selected from the group consisting of crosslinked acrylic homopolymers or copolymers and 0.05% to 10% of at least one lamellar or platelet-shaped matting mineral filler, wherein the at least one lamellar or platelet-shaped matting mineral filler is a member selected from the group consisting of perlite and expanded perlite and mixtures thereof, and the at least one superabsorbent polymer is, in dry form, in the form of particles with a weight-average size of less than or equal to 100 μm, and wherein the composition is in the form of an oil-in-water emulsion or a water-in-oil emulsion.

2. The composition according to claim 1, in which the at least one superabsorbent polymer is, once hydrated, in the form of particles with a weight-average size ranging from 10 µm to 1000 µm.

3. The composition according to claim 1, in which the at least one superabsorbent polymer has a capacity to absorb water at 0.9% of NaCl from 10 to 100 g/g.

4. The composition according to claim 1, in which the at least one superabsorbent polymer is chosen from crosslinked sodium polyacrylates.

5. The composition according to claim 1, in which the at least one superabsorbent polymer is in the form of spherical particles.

6. The composition according to claim 1, in which the at least one lamellar or platelet-shaped matting mineral filler is solid mineral particles with a refractive index of less than or equal to 1.55.

7. The composition according to claim 6, in which the length of the particles ranges from 0.01 to 100 µm, and their height (thickness) ranges from 0.1 nm to 1 µm (0.1 to 1000 nm).

8. The composition according to claim 1, in which the at least one lamellar or platelet-shaped matting mineral filler is chosen from particles with a water absorption capacity, measured at the wet point, of greater than or equal to 100 g.

9. The composition according to claim 1, in which the at least one superabsorbent polymer is, in dry from, in the form of particles with a weight-average size of less than or equal to 50 µm.

10. The composition according to claim 1, in which the at least one superabsorbent polymer, once hydrated, in the form of particles with a weight-average size ranging from 20 µm to 500 µm.

11. The composition according to claim 1, in which the at least one superabsorbent polymer is an acryloacrylamide/sodium acrylate copolymer.

12. The composition according to claim 6, wherein said crosslinked acrylic homopolymers or copolymers is a neutralized crosslinked acrylic homopolymer or copolymer.

13. The composition according to claim 6, in which the length of the particles ranges from 0.1 to 50 µm and their height (thickness) ranges from 1 nm to 600 nm.

14. The composition according to claim 1, in which the at least one lamellar or platelet-shaped matting mineral filler is chosen from particles with a water absorption capacity, measured at the wet point, ranging from 200% to 1500%.

15. A composition for making up facial skin to impart a matt appearance to the facial skin comprising:
at least one aqueous phase;
0.05% to 15% of at least one superabsorbent polymer that is crosslinked acrylic homopolymer or copolymer, wherein the at least one superabsorbent polymer is, in dry form, in the form of particles with a weight-average size of less than or equal to 100 µm;
0.05% to 10% of at least one lamellar or platelet-shaped matting mineral filler selected from the group consisting of perlite, expanded perlite, and mixtures thereof;
wherein the composition is in the form of an oil-in-water emulsion or a water-in-oil emulsion, and the composition provides a matt appearance to the facial skin.

16. The matt composition of claim 15, further comprising:
at least one linear or branched lower monoalcohols containing from 1 to 8 carbon atoms.

17. A cosmetic process for treating a keratin material, in which a cosmetic composition as defined in-claim 1 is applied to the keratin material.

* * * * *